United States Patent [19]
Cooper et al.

[11] Patent Number: 5,788,364
[45] Date of Patent: Aug. 4, 1998

[54] COMPACT HIGH-INTENSITY UVA INSPECTION LAMP

[75] Inventors: B. William Cooper, Lloyd Harbor; Gustavo Garcia, Lake Grove; Richard Regan, Short Hills, all of N.Y.

[73] Assignee: Spectronics Corporation, Westbury, N.Y.

[21] Appl. No.: 888,722

[22] Filed: Jul. 7, 1997

Related U.S. Application Data

[62] Division of Ser. No. 496,076, Jun. 28, 1995.

[51] Int. Cl.⁶ ............................................. F21V 9/00
[52] U.S. Cl. ................ 362/293; 362/294; 362/264; 362/373; 362/399; 250/504 H
[58] Field of Search ............................ 362/263, 264, 362/293, 294, 343, 345, 373, 399; 250/504 H

[56] References Cited

U.S. PATENT DOCUMENTS

| 4,298,806 | 11/1981 | Herold | 250/504 H |
| 5,050,055 | 9/1991 | Lindsay et al. | 362/293 |

*Primary Examiner*—Stephen F. Husar
*Attorney, Agent, or Firm*—Seidel Gonda Lavorgna & Monaco, PC

[57] ABSTRACT

A compact hand-held high intensity ultraviolet inspection lamp having a straight handle aligned with beam direction includes a high-intensity light bulb enclosed within a bulb housing, a light-emitting aperture at the end of the bulb housing away from the handle, and an ultraviolet light filter in alignment with the aperture to absorb substantially all light emitted from the bulb at frequencies outside of the ultraviolet spectrum and to transmit the unabsorbed ultraviolet light. Three embodiments of such lamp are disclosed herein.

9 Claims, 6 Drawing Sheets

5,788,364

COMPACT HIGH-INTENSITY UVA INSPECTION LAMP

This is a divisional of copending application Ser. No. 08/496,076 filed on Jun. 28, 1995.

FIELD OF THE INVENTION

The invention is directed to the general field of hand-held lamps, and to the particular field of hand-held ultraviolet inspection lamps for UVA illumination in the detection of fluorescent materials.

BACKGROUND OF THE INVENTION

It is a well-known phenomena that electromagnetic radiation within the near ultraviolet, or "UVA" spectrum of approximately 315 to 400 nanometer wavelength produces fluorescence in certain materials. That is, the fluorescent materials absorb radiated energy at the UVA wavelength and re-radiate it at a longer wavelength in the visible spectrum. This phenomena has enabled inspection and detection techniques in which fluorescent dyes, inks or paints are illuminated by lamps selectively filtered to emit only ultraviolet radiation (often called "black light" because little visible spectrum light escapes the filter), and then re-radiate with a high luminescence in the visible spectrum. These techniques are used extensively in non-destructive testing, leak detection and security systems.

For example, the slow leakage of refrigerant from an air conditioning system is difficult to locate by any other means, because the refrigerant escapes as an invisible gas at such low rate and rapid diffusion that the concentration of refrigerant in air near the leak site is difficult to differentiate from that surrounding any other location along the system circulation lines. However, by infusing into the circulating system a small amount of fluorescent dye which is soluble in the refrigerant, the dye is carried out of the system with the refrigerant, and glows brightly at the leak site when the area is swept with a UVA lamp. A similar procedure can be used to locate leaks of other fluids, such as lubricant oils, fuels, heat transfer fluids or hydraulic fluids. Other UVA inspection techniques use fluorescent dyes or paint to detect fissures or stress cracks in structural members.

Where an inspection for leaks, cracks or fissures is conducted in confined or difficult to reach spaces, it would be advantageous to use a compact, hand-held lamp. It would also be an advantage for maneuverability and for insertion through narrow spaces to have the lamp's handle aligned with the beam direction, as in a traditional in-line flashlight. However, a compact lamp must be capable of radiating UVA radiant flux sufficient to produce, at a distance of about eight to thirty inches from the lamp, a fluorescent response in the detector material to re-radiate sufficient lumens to be easily sighted by the inspector.

A compact, hand-held, high intensity ultraviolet inspection lamp has not previously been developed, and apparently has been regarded as impractical, due to the large amount of heat developed by the high intensity source bulbs and the UV filters which are required to produce a sufficient flux of UVA emission from the lamp. As a general proposition, incandescent lamps with higher filament temperatures radiate a greater percentage of light in the ultraviolet range than do cooler filaments. Thus, a high-temperature tungsten halogen lamp is well suited for a UVA light source, but it simultaneously produces much direct heat and visible light radiation. Arc discharge lamps which emit a substantial percentage of ultraviolet radiation, such as mercury vapor lamps and metal halide lamps, also operate at high temperatures.

Moreover, even given that a larger percentage of ultraviolet radiation is emitted from hotter lamps, the light which is radiated from the lamp in the visible spectrum must be blocked from emission by a selective filter, which absorbs and converts visible light into heat while transmitting the ultraviolet radiation.

Thus, there are typically at least two heat sources to consider in designing a compact hand-held UVA lamp; the light source itself and the UV filter. Moreover, the focusing reflector may selectively reflect UV while absorbing visible radiation, becoming a third heat source. If these heat-generating components are located in close proximity to each other in a compact, hand-held lamp, the combined heat is likely to produce unsafe temperatures in the lamp housing, thus creating a potential hazard for severe burns to an operator, or causing components to deform, fracture, or otherwise prematurely fail. Since the compact lamp's handle is located close to the heat-generating components, heat conducting back from the housing to the handle may make the handle uncomfortably hot if the lamp is operated for more than a brief interval.

Despite these difficulties, a compact, high intensity UVA inspection lamp would have great appeal to several industries which use UVA light in maintenance or inspection processes. Contemporary UVA lamps of sufficient power to be considered high intensity tend to incorporate large bulbs, external heat guards, bulky bulb housings, and pistol-type handles which are off-set from the beam direction. These large lamp assemblies can absorb and dissipate internal heat over a considerable surface area of the lamp assembly, thereby producing relatively mild temperatures on the external surfaces.

These larger UV lamps tend to obstruct the users' view of the components being inspected, and their size may prevent the user from bringing the lamp close to components of complicated machinery or from inserting it into areas which are difficult to reach. This can limit the effectiveness of a UVA inspection.

Accordingly, there is a need for a compact, in-line, hand-held UVA inspection lamp that can be used in tight spaces and maneuvered to illuminate the parts to be inspected. This compact UVA light source must have sufficient UVA emission, yet be capable of dissipating the heat generated by producing that UVA emission without creating discomfort or hazard to operators, or failure of its component parts. It is an object of this invention to provide a lamp having this capability.

SUMMARY OF THE INVENTION

A compact hand-held high intensity ultraviolet inspection lamp having a straight handle aligned with beam direction includes a high-intensity light bulb enclosed within a bulb housing, a light-emitting aperture at the end of the bulb housing away from the handle, and an ultraviolet light filter in alignment with the aperture to absorb substantially all light emitted from the bulb at frequencies outside of the ultraviolet spectrum and to transmit the unabsorbed ultraviolet light.

Three embodiments of such lamp are disclosed herein.

In one embodiment, the bulb housing comprises a curved metal dish, with an integral internal surface that is polished and shaped as a focusing reflector, and a generally cylindrical extension to increase heat dissipation area. The UV filter is recessed in an elastomeric holder which is attached to the housing extension.

In a second embodiment, the bulb housing comprises a curved dish made of a plastic or other heat insulating material, with a separate internal focusing reflector. An electrical socket internally mounted in the handle receives the base of the high-intensity light bulb such that the filament portion of the bulb extends into the bulb housing. A heat barrier wall and insulating chamber is provided between the socket and the grip portion of the handle. The UV filter is recessed in an elastomeric holder which is attached to the housing.

In both of the above embodiments, a small circular scattering reflector may be mounted at the center of the inner surface of the UV filter to reflect incident light back onto the focusing reflector, thus eliminating what would otherwise be a hot spot at the center of the filter.

In a third embodiment, the bulb housing is a cylindrical chamber aligned with and connected to the handle by a small-diameter hollow tube. A light guide extends from the aperture in the housing. The bulb housing contains the light source and a UV dichroic focusing reflector, which focuses UVA light into the input end of light guide. The UV filter is provided at the terminal end of the light guide.

In all three embodiments, the lamp may have an electrical transmission line running internally within the handle to connect the bulb to a power source.

DETAILED DESCRIPTION OF THE INVENTION AS SHOWN IN THE DRAWINGS

A compact, hand-held, high intensity UVA inspection lamp with a straight handle aligned with the beam direction is made feasible by solving the problems associated with the heat generated by the high intensity light source and the UV filter.

Figure 1:
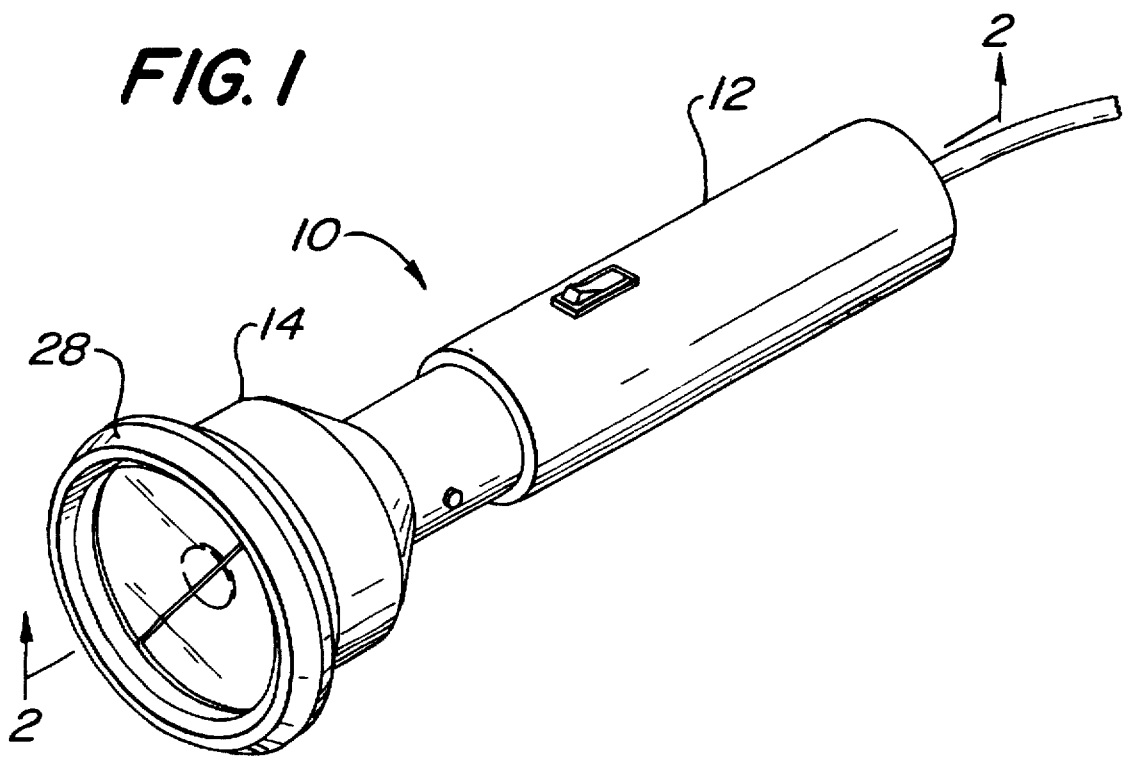
FIG. 1 is a perspective view of an embodiment according to the invention in which an integral metal bulb housing is used.

As depicted in FIG. 1, a compact, hand-held, high intensity UVA inspection lamp 10 has a straight handle 12, and a bulb housing 14 to enclose and protect a high intensity light source and a focusing reflector. As better seen in the sectional view of FIG. 2, the handle is a cylindrical tube with generally circular cross-section, and therefore a concentric longitudinal axis, and has a closed butt-end 16 and an open opposite end 18. A grip area of the handle is determined by the placement of an ON/OFF momentary control switch, which is manipulated by the thumb. Other in-line handle shapes which are modified to provide a comfortable grip can be used, but the longitudinal axis of the handle should be substantially aligned with the beam direction to provide a narrow profile for insertion into tight areas and enable instinctive pointing of the beam.

The bulb housing is an enclosed chamber attached to one end of the handle in a fixed in-line attachment such that the longitudinal axis of the housing is substantially aligned with the axis of the handle. A high-intensity light source is located inside the housing. A presently preferred light source is a 50–75 watt tungsten halogen bulb 20 having a two-pin base, although other types and power ratings of high intensity bulbs could be used. Within the housing is a focusing reflector 22, having a conic section selected for focusing the light emitted from the bulb. The bulb is mounted such that the light source essentially encompasses the focus or foci of the reflector.

In the embodiments depicted in FIGS. 1–5, the preferred contour of the reflecting surface is a hybrid conic section selected to focus the UVA light at approximately eighteen inches from the bulb, which converges the light into a beam of sufficient intensity at convenient working distances for most UVA fluorescent inspections. In the embodiment depicted in FIGS. 6–8, the reflector contour is selected to produce a close-in convergence into a light guide, as described in greater detail later in this text.

An aperture 24 is located in the bulb housing at the end of the housing opposite the focusing reflector. An ultraviolet filter 26 is mounted in alignment with the aperture by a filter holder 28. An ultraviolet or UV filter is a device which absorbs substantially all incident light in the visible spectrum, while transmitting a substantial portion of incident light in at least some band of the UVA spectrum. Such filters are well known and often referred to as "black light" filters. Thus, the filter absorbs light emitted from the bulb at visible and other wavelengths, but transmits ultraviolet light in the UVA spectrum.

Each of the embodiments described herein have one or more features which isolate enough of the heat generated by the bulb and filter from conduction to the grip area of the handle to prevent the handle from becoming uncomfortably hot during use. These design feature may dissipate or distribute the heat, or otherwise isolate the heat sources from high conduction paths to the grip portion of the handle. Such features may be used in various combinations. In the embodiments depicted in FIGS. 1–5, the UV filter is separated from the light source by a short distance, essentially the length of the housing. These embodiments may need additional design features to protect the filter itself from damage due to overheating. These various features will be described as they appear in the three embodiments depicted in this specification.

Figure 3:
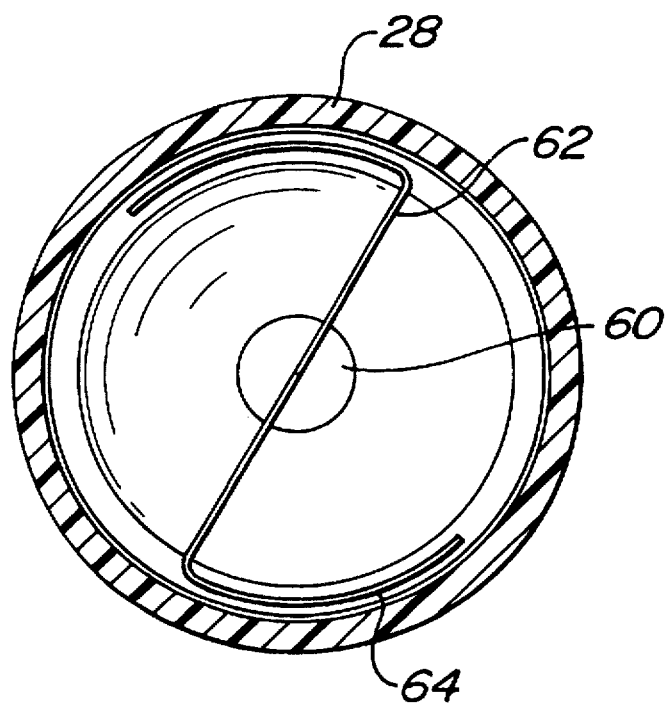
FIG. 3 is a section view of the embodiment of FIG. 1 along the line and in the direction of the indicator arrows 3—3 on FIG. 2.
Figure 2:
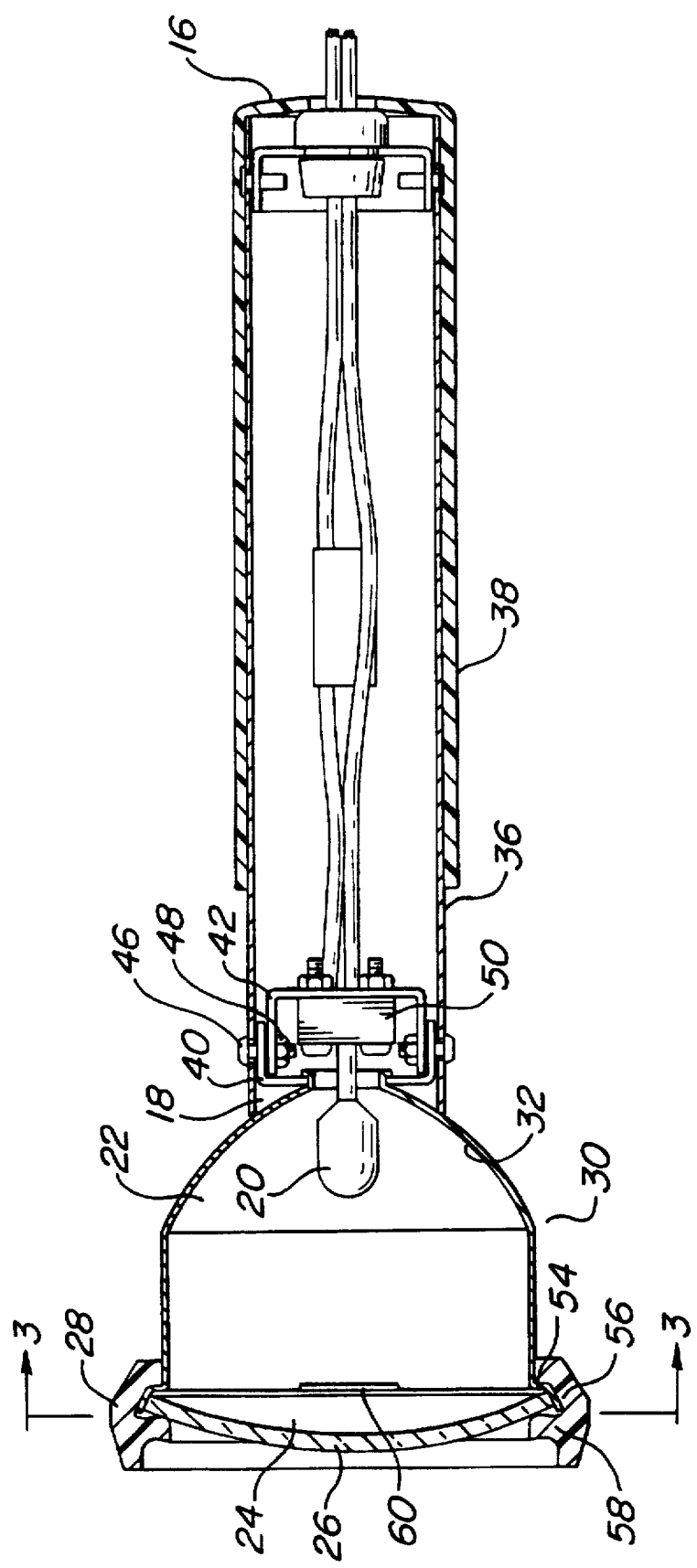
FIG. 2 is a section view of the embodiment of FIG. 1 along the line and in the direction of the indicator arrows 2—2.

In the embodiment of FIGS. 1–3, an integral metal structure 30 forms the bulb housing 14, with the focusing reflector 22 being a highly polished and properly contoured inner surface 32 of the housing. The integral metal housing continues beyond the reflector surface to form a generally cylindrical extension 34. This extended reflector-housing, made of heat conductive metal, increases the effective heat dissipation area of the housing to the ambient environment and permits an intense light source to be enclosed in a small unit.

The handle 12 is a metal tube 36 with an insulating sleeve 38 over the grip area. A circular housing bracket 40 is crimp-mounted to the base of the bulb housing, and has a diameter such that it makes a snug conformal fit into the open end 18 of the metal tube. A circular socket bracket 42 is sized for a conformal fit inside the rim of the housing bracket 40. Both brackets have fastener holes located to align with its counterpart of the other bracket. The handle tube 36 has a set of matching fastener holes to align with the holes in the brackets and permit the parts to be joined by fasteners. In the embodiment depicted, the fasteners are machine screws 46, and a threaded nut 48 is attached below each hole in the socket bracket to engage the screw threads.

A two-pin bulb socket 50 is mounted in the socket bracket, and arranged such that the tungsten filament/halogen capsule portion of the bulb extends through the housing and is located to encompass the focus or foci of the reflector when the parts are assembled. The bulb can be removed and replaced by removing the filter holder, extracting the spent bulb from the socket and inserting a fresh bulb, and replacing the filter holder.

The circular open end 18 of the handle tube matches the outside contour of the housing such that the tube provides full contact to the housing around its circumference, making the attachment stable. A beneficial result of the small contact area between handle and housing is that the heat absorbed in the bulb housing does not have a large conductive path back through the handle. The insulating sleeve 38 protects the grip portion of the handle against heat which does conduct backward.

A momentary ON/OFF switch 52 takes advantage of the halogen tungsten bulb's ability to produce intense radiation without a warm-up period. This allows a user to turn the lamp on only when the UVA illumination is wanted, limiting the time during which any heat will be generated.

The filter holder 28 is formed of silicone or another elastomer. The bulb housing extension flares outward at the aperture end to form a skirted flange 54. The filter holder has an interior notch 56 contoured for conformal fit around the housing flange. The filter holder also has a hook ring 58 above the notch to retain the UV filter securely. The internal hook design of the holder permits filters of varying thickness to be used. Although the UV filter may have a convex lens shape as depicted in FIG. 2, the filter holder extends beyond the hook ring and terminates in a flat face ring 59 such that the entire filter is recessed in the holder. This permits the elastomeric holder to act as a shock absorber, and to be used as a stand, allowing the lamp to be stored in an upright position resting on the flat face ring of the holder.

To protect the UV filter from heat damage, a scattering reflector disk 60 is provided between the bulb and the center of the UV filter. Because both direct light from the bulb and converging light from the focusing reflector are directed at the center, the light intensity at the center of the filter would be substantially greater than at the filter's periphery, with graduated intensity in between, creating a "hot spot" at the center region. By locating the scattering reflector in front of that point, the light is scattered back onto the focusing reflector from outside the reflector's focal point, and is then re-reflected in a more random and even distribution onto the UV filter. The effect is a more even distribution of light, and thus heat, across the filter surface, eliminating the hot spot.

The scattering reflector disk is attached to a thin wire support 62, with ends 64 of the support curved to match the circumference of the skirted flange of the housing. Thus, the ends lie under the edge of the UV filter and are held in place by the filter holder.

A electrical power cord 66 connects the lamp to an electrical power source. The handle receives the cord line at the closed butt-end, and the wire leads of the cord run through the handle to the bulb socket.

Figure 5:
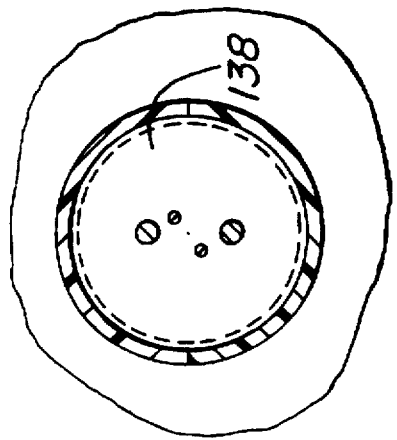
FIG. 5 is a section view of the full embodiment depicted in FIG. 4 along the line and in the direction of the indicator arrows 5—5.
Figure 4:
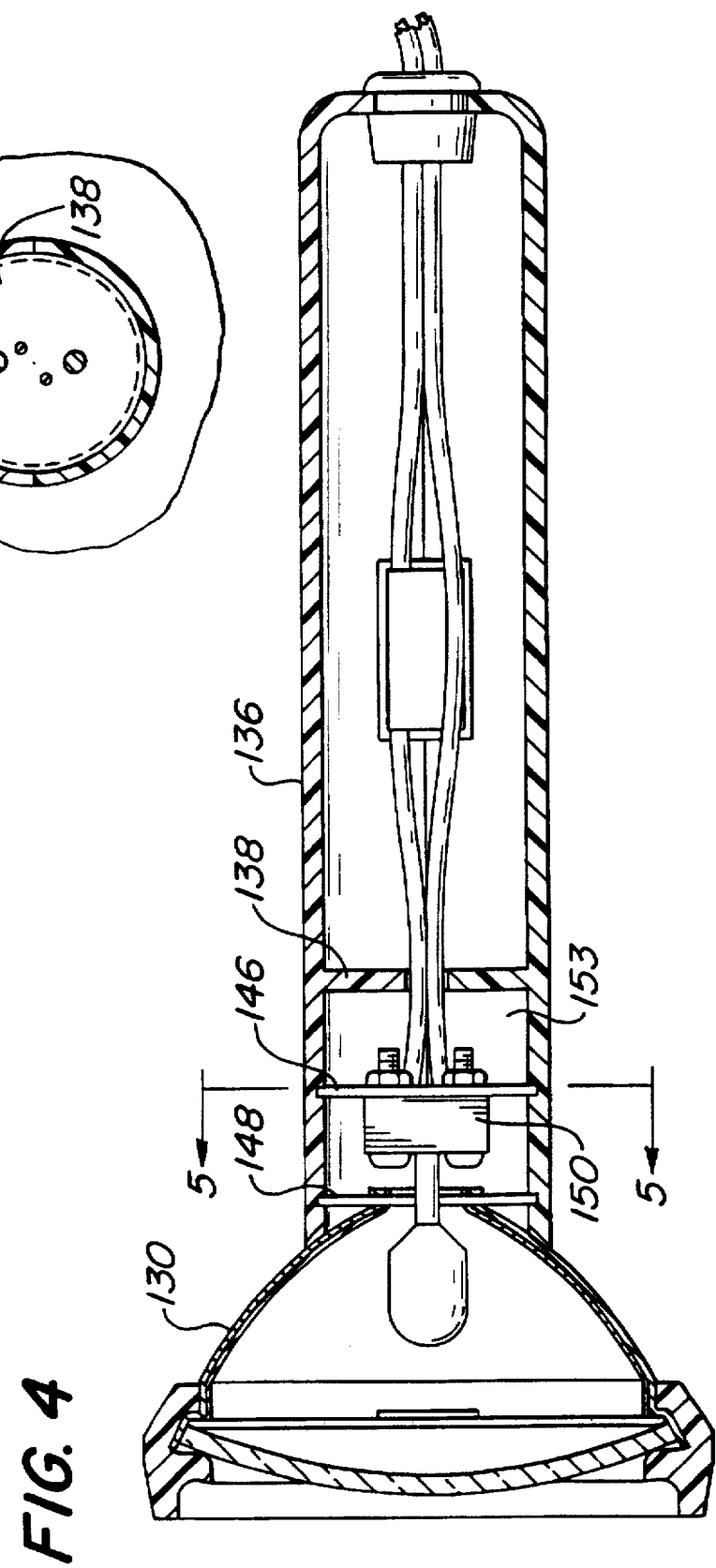
FIG. 4 is a section view of another embodiment according to the invention, in which a plastic bulb housing is used.

In the embodiment of FIGS. 4 and 5, the bulb housing 130 is a curved structure made of low-conductivity material, such as high-temperature resistant plastic. Inside the housing is a separate focusing reflector 132 made of polished metal. The distance between bulb and UV filter is short in this embodiment, and a substantial amount of heat generated therein is contained in the housing rather than dissipated or distributed. Consequently, in this embodiment one or more other features, as described herein, should be used to isolate the heat from the grip portion of the handle and to protect the UV filter from hot spots.

The handle 136 may also be constructed of a high temperature resistant plastic with low heat conductivity, which will insulate and reduce the heat transfer from the lamp-reflector-filter assembly to the grip portion of the handle. As depicted in the exploded view of FIG. 6, the cylindrical handle is formed from two essentially identical, hemispherical-split sub-assemblies 136a–136b, which are bonded together after assembly of the internal parts. Each sub-assembly has an internal wall section 138a–138b, which, when the sub-assemblies are joined, forms a heat barrier wall 138 with a central opening only large enough for the electrical wires.

Each sub-assembly also has two inner-circumferential slots which match when assembled to form circumferential grooves to hold mounting brackets. Into the slot 142 closest to the open end of the handle is inserted a housing mounting bracket 144. The bulb housing and reflector are crimp mounted to the housing mounting bracket, which permits the bulb to be inserted through both reflector and housing. The open circular end of the handle is chamfered to match the outside contour of the housing such that it provides full contact to the housing and results in additional stability to the connection.

Into the next slot 146 is inserted a socket mounting bracket 148. A two-pin bulb socket 150 is mounted in the socket mounting bracket and arranged such that the tungsten filament/halogen capsule portion of the bulb extends through the housing and is located to encompass the focus or foci of the reflector when the parts are assembled.

As shown in FIG. 5, the socket mounting bracket is essentially a solid disk with holes only to pass the electrical wires and to receive the socket attachment screws, and forms an air barrier behind the lamp socket. Thus, the hollow area between the socket mounting bracket and the heat barrier wall forms a dead air insulating chamber 153 ahead of the grip portion of the handle.

A momentary switch 152 is used to take advantage of the tungsten halogen bulb's ability to produce intense radiation without a warm-up period. Also, as in the previous embodiment, a scattering reflector disk 160 is provided at the center of the UV filter to protect the UV filter from heat damage. The filter holder is essentially identical to that of the embodiment of FIGS. 1–3 described above.

Figure 6:
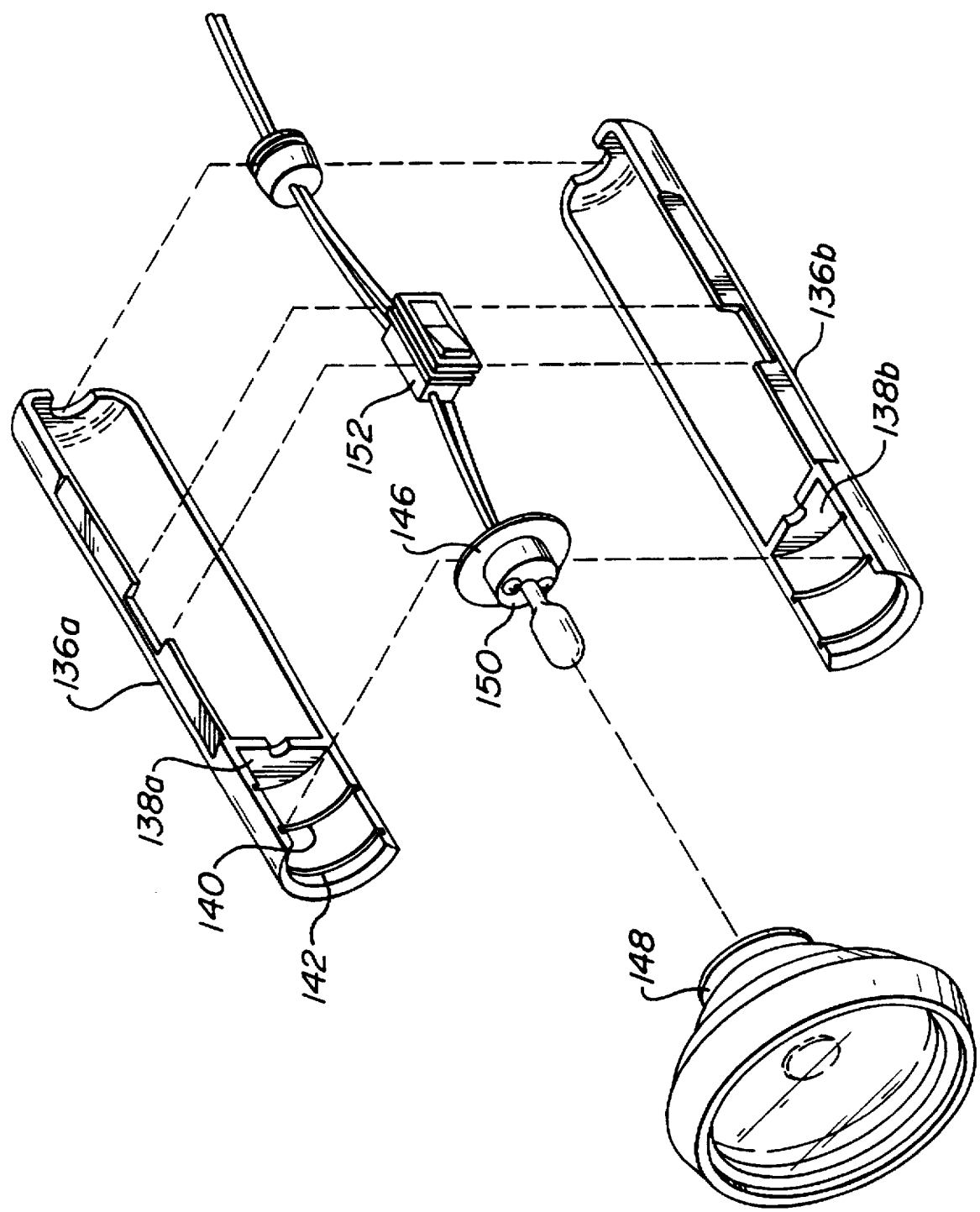
FIG. 6 is an exploded view of the full embodiment depicted in FIG. 4.
Figure 7:
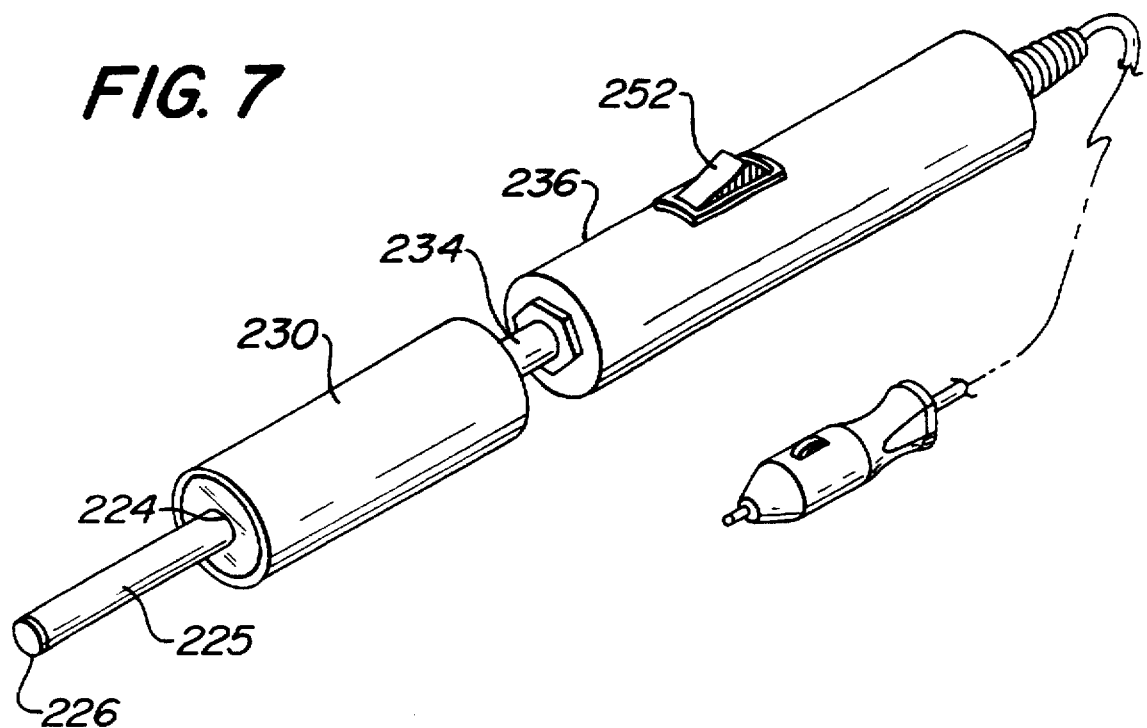
FIG. 7 is a perspective view of a third embodiment according to the invention, in which a light guide terminating in a UV filter extends from the bulb housing.
Figure 9:
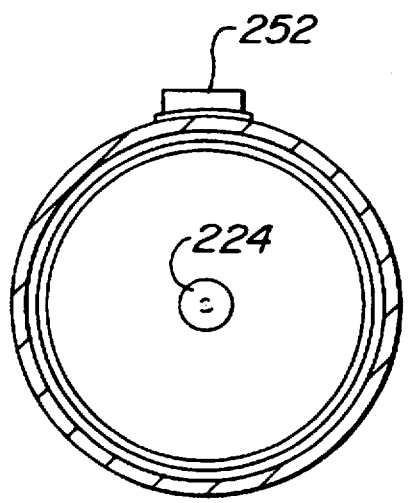
FIG. 9 is a section view of the full embodiment depicted in FIG. 7 along the line and in the direction of the indicator arrows 8—8 of FIG. 8.
Figure 8:
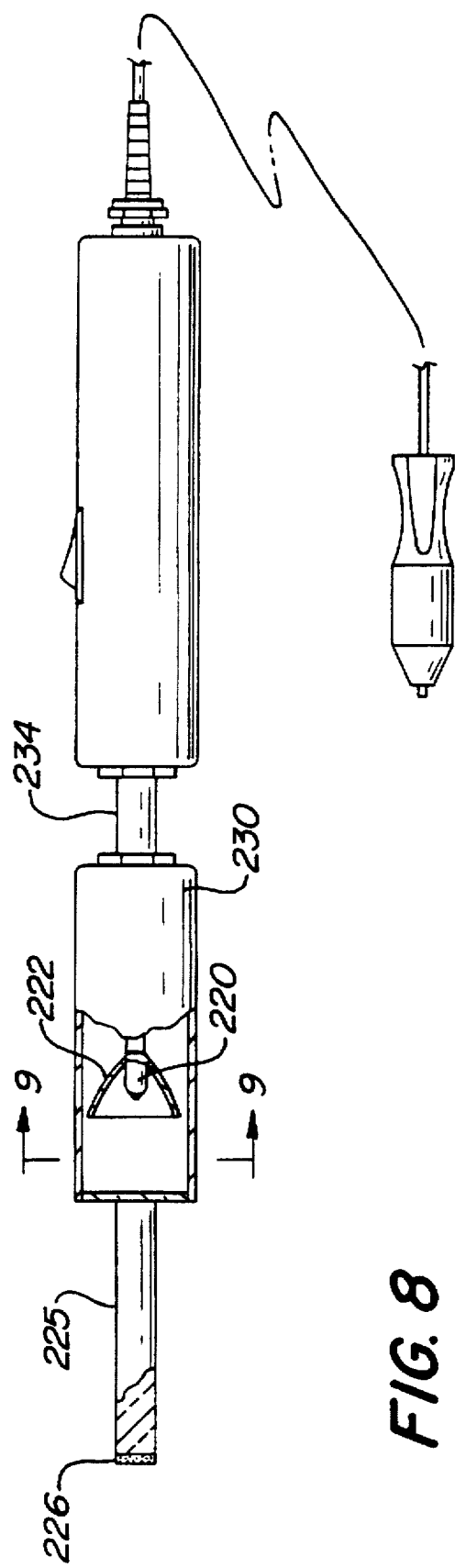
FIG. 8 is a section view of the embodiment of FIG. 7.

In the embodiment of FIGS. 6–8, the bulb housing is a closed cylindrical chamber 230 separated from and connected to the handle 236 by a small diameter hollow tube 234. At the opposite end of the housing is an aperture 224 into which is mounted the receiving end of a light guide 225. The focusing reflector 222 of this embodiment is a UV dichroic reflector mirror, mounted around the bulb 220 and having a contour selected to converge a beam of the incident UVA light into the light guide. The radiation incident on the reflector below the UVA frequency is transmitted through the dichroic material to the walls of the chamber where it is absorbed, and the absorbed heat is then dissipated over the external surface of the chamber.

Thus, most of the visible light is absorbed by the walls of the housing chamber, while the UV light is directed out through the light guide. The heat produced by the light source and absorbed by the chamber walls is isolated from the handle by the small heat conduction area of the hollow tube 234.

The light guide may have a solid core of optical glass up to approximately one-half inch diameter with a drawn clad coating. The light guide channels the reflected UV and a small amount of direct visible light to the UV filter 226 which absorbs the visible light and transmits the UVA light. Since the filter is located a fair distance from the light source and is not in an enclosed chamber with the light source, it is subjected to little direct heat from the source. The filter experiences only the heat it generates by absorbing the small amount of visible light which enters the input end of the guide, which it can dissipate without causing damage to itself.

The light guide portion can be made in various shapes and lengths to direct the UVA light into a difficult to access position, and can be flexible within limits. The filter end may have a selection of end fittings or lenses to converge or diverge the emitted UVA light and to protect the guide and filter.

As in the other embodiments, a momentary switch 152 is used to take advantage of the halogen tungsten bulb's ability to produce intense radiation without a warm up period.

We claim:

1. A hand-held high intensity ultraviolet inspection lamp comprising:
   a) a substantially-straight handle having two ends, a grip area, and a longitudinal axis;
   b) a bulb housing comprising an enclosed chamber attached to one end of the handle, said bulb housing also having a longitudinal axis, and said handle and said bulb housing being in a fixed in-line attachment such that the axis of the housing is substantially aligned with the axis of the handle;
   c) a high-intensity light bulb within the bulb housing;
   d) an aperture in the bulb housing located along the longitudinal axis of the housing at the end of the housing opposite the handle,
   e) a focusing reflector inside the bulb housing,
   f) an ultraviolet light filter positioned to block the emission of visible light from the lamp; and
   g) means for isolating heat generated by the bulb from heat generated by the ultraviolet filter, and for isolating the heat from both sources from conduction to the grip area of the handle.

2. A lamp as in claim 1, comprising:
   a) the bulb housing is a generally cylindrical hollow chamber connected to the handle by a small diameter hollow tube;
   b) a light guide extending from the aperture of the bulb housing; and
   c) the ultraviolet filter is provided at the end of the light guide.

3. A lamp as in claim 2, wherein the focusing reflector is an UVA dichroic reflector mirror mounted around the bulb and having a contour selected to converge a beam of incident UVA light into the light guide.

4. A lamp as in claim 3, wherein the dichroic reflector mirror passes radiation below the UVA frequency through the dichroic material to the interior surface of the hollow chamber where it is absorbed, and the absorbed heat is dissipated over the external surface of the chamber.

5. A lamp as in claim 2, further comprising a transmission line connecting the bulb to an electrical power source, the handle being adapted to receive the transmission line at the handle end opposite the end to which the bulb housing is connected.

6. A lamp as in claim 3, further comprising a transmission line connecting the bulb to an electrical power source, the handle being adapted to receive the transmission line at the handle end opposite the end to which the bulb housing is connected.

7. A lamp as in claim 4, further comprising a momentary on/off switch in the handle.

8. A lamp as in claim 5, further comprising a momentary on/off switch in the handle.

9. A lamp as in claim 6 further comprising a momentary on/off switch in the handle.

* * * * *